United States Patent
Kamel

(10) Patent No.: US 8,613,752 B2
(45) Date of Patent: Dec. 24, 2013

(54) SURGICAL INSTRUMENT FOR REMOVING BODY TISSUE OR VESSELS

(75) Inventor: Amro Kamel, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 202 days.

(21) Appl. No.: 13/091,684

(22) Filed: Apr. 21, 2011

(65) Prior Publication Data

US 2012/0271332 A1    Oct. 25, 2012

(51) Int. Cl.
*A61B 17/3201* (2006.01)
*A61B 17/285* (2006.01)

(52) U.S. Cl.
USPC .......................................... 606/174; 606/205

(58) Field of Classification Search
USPC ................... 606/37, 39, 45, 49, 52, 167, 174, 606/205–208
See application file for complete search history.

(56) References Cited

U.S. PATENT DOCUMENTS

| | | | |
|---|---|---|---|
| 2,002,594 A | 5/1935 | Wappler et al. | 174/89 |
| 2,031,682 A | 2/1936 | Wappler et al. | 174/89 |
| 4,655,216 A | 4/1987 | Tischer | 128/303.17 |
| 5,772,576 A | 6/1998 | Knighton et al. | 600/36 |
| 5,800,449 A | 9/1998 | Wales | 606/172 |
| 5,913,866 A | 6/1999 | Ginn et al. | 606/174 |
| 5,964,758 A | 10/1999 | Dresden | 606/45 |
| 6,019,771 A | 2/2000 | Bennett et al. | 606/159 |
| 6,142,994 A | 11/2000 | Swanson et al. | 606/41 |
| 6,358,268 B1 | 3/2002 | Hunt et al. | 606/206 |
| 6,425,896 B1 | 7/2002 | Baltschun et al. | 606/51 |
| 6,497,651 B1 | 12/2002 | Kan et al. | 600/114 |
| 6,527,767 B2 | 3/2003 | Wang et al. | 606/32 |
| 6,676,660 B2 | 1/2004 | Wampler et al. | 606/51 |
| 6,743,230 B2 | 6/2004 | Lutze et al. | 606/51 |
| 7,699,861 B2 | 4/2010 | Bayer | 606/159 |
| 7,815,641 B2 | 10/2010 | Dodde et al. | 606/51 |
| 2001/0014805 A1* | 8/2001 | Burbank et al. | 606/45 |
| 2008/0312653 A1 | 12/2008 | Arts et al. | 606/51 |

FOREIGN PATENT DOCUMENTS

GB    2082459 A    3/1982    ............. A61B 17/32

* cited by examiner

*Primary Examiner* — Ryan Severson
(74) *Attorney, Agent, or Firm* — Brinks Gilson & Lione

(57) ABSTRACT

A surgical instrument and a method for using the instrument are provided. The instrument can include a tubular member. A grasper can extend within the tubular member. The grasper can have grasping members each with a distal body. An opening can be formed in an inner surface of each distal body. The grasping members can pivot between an open and a closed configuration to engage a body vessel or tissue. A cutting device can extend within the tubular member. The cutting device can have a cutting member with a cutting edge. The cutting member can be movable between a free and an engaged configuration to sever a body vessel or tissue. When the grasping members are in the closed configuration, the openings of the distal bodies can form a cavity to receive the cutting member to shield the cutting member during navigation within a body of a patient.

16 Claims, 4 Drawing Sheets

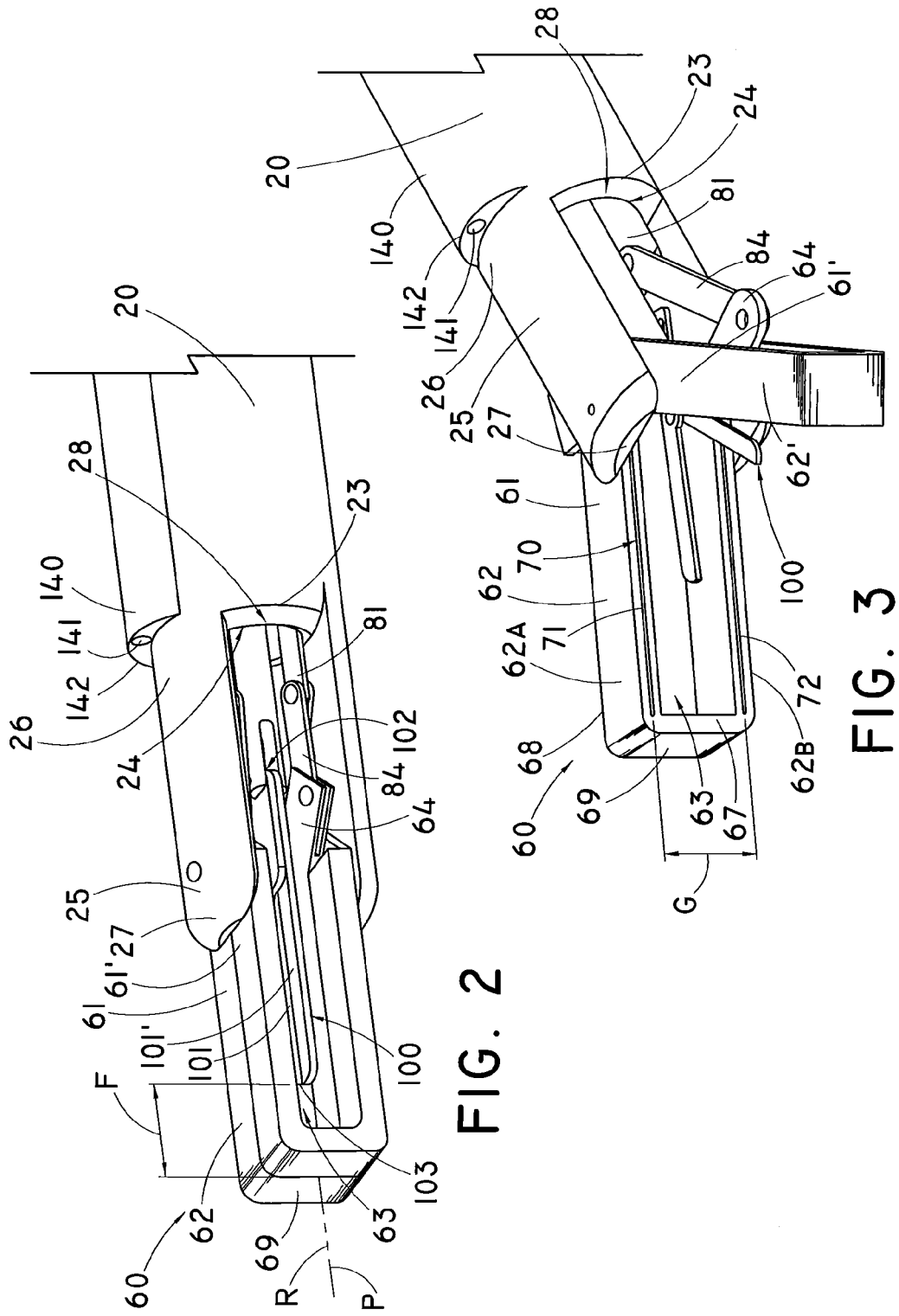

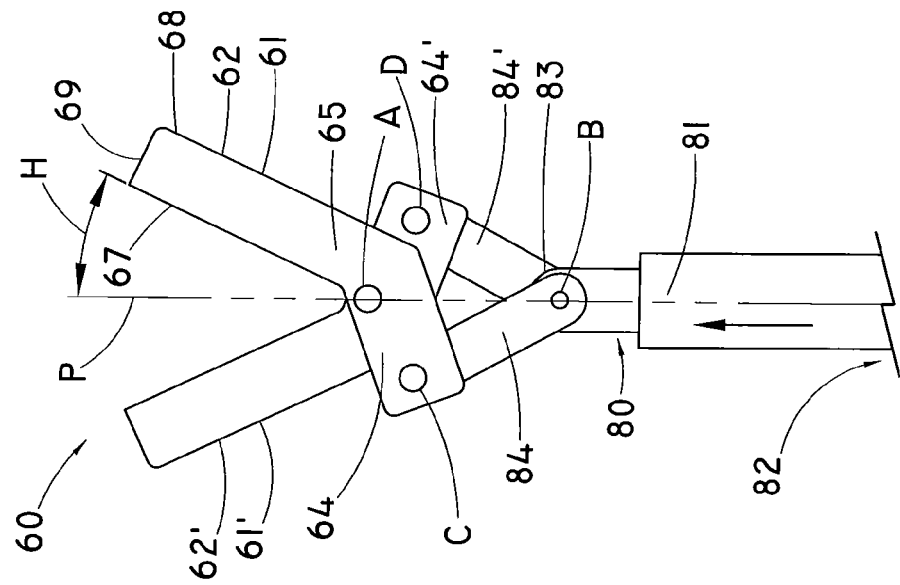
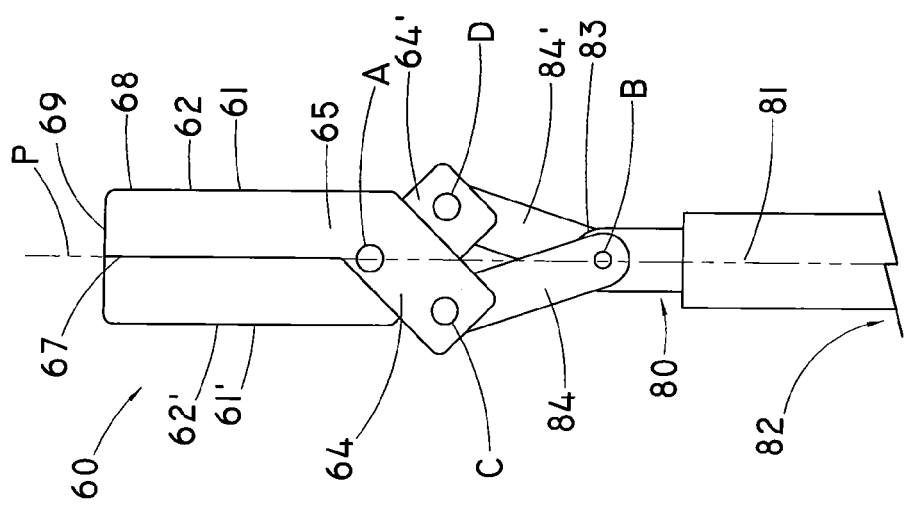
FIG. 4B
FIG. 4A

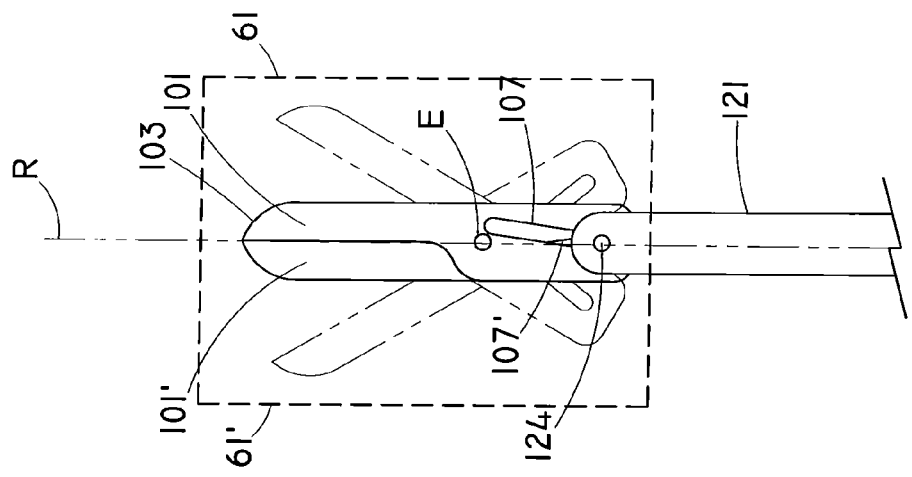
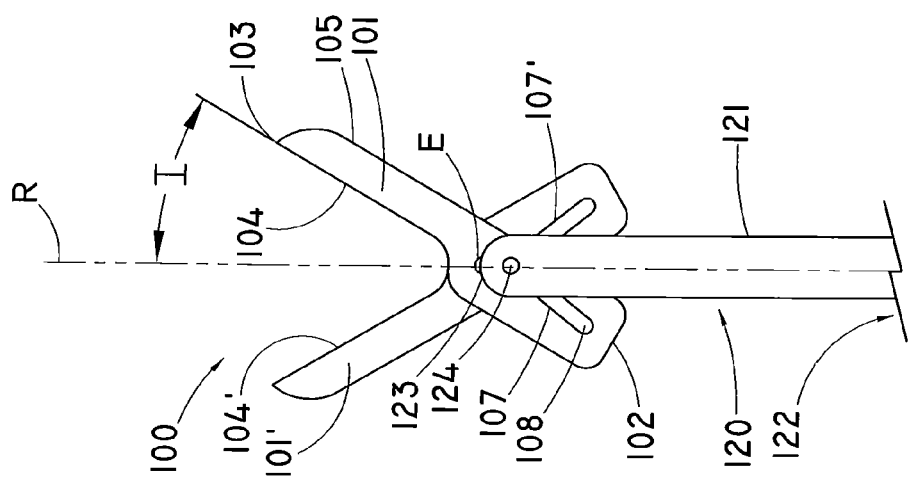
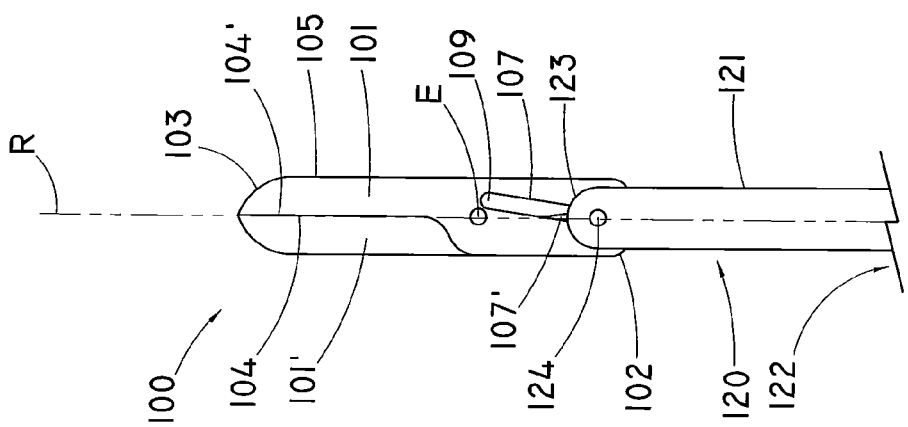

SURGICAL INSTRUMENT FOR REMOVING BODY TISSUE OR VESSELS

TECHNICAL FIELD

The present disclosure relates generally to medical devices and methods of use. More particularly, it relates to surgical instruments, such as endoscopic or laparoscopic instruments, for removing body tissue or vessels, such as saphenous veins for use in coronary artery bypass surgery.

BACKGROUND

Coronary artery disease is often characterized by lesions or occlusions in the coronary arteries. This disease may result in inadequate blood flow to the myocardium, or myocardial ischemia, which is typically responsible for complications such as angina pectoris, necrosis of cardiac tissue (myocardial infarction), and sudden death. Drugs and/or modifications in behavior and diet may be used to treat coronary artery disease. Other types of treatment include dilation of coronary arteries by procedures such as angioplasty, laser ablation, atherectomy, catheterization, and implantation of intravascular stents. In more severe cases, coronary bypass surgery may be required when other methods of treatment are impossible for a variety of reasons or ineffective in clearing the occluded artery.

Coronary artery bypass graft (CABG) surgery is one type of coronary bypass surgery. In CABG surgery, a blood vessel is obtained from another portion of the patient's body and used to create a bypass conduit around the occlusion to restore proper blood flow through the coronary artery. A common blood vessel for use in such procedures is the saphenous vein which is located in a patient's leg. The saphenous vein is preferred because it is found close to the surface of the skin and requires minimal dissection to harvest, or extract, from the body.

The blood vessel selected for extraction typically has a plurality of vessels branching from the blood vessel. Dissection of branching vessels from the blood vessel often is required to ultimately extract the blood vessel. To dissect the branching vessels, each of the branching vessels must be severed with a cutting device and burnt shut, or cauterized, to stop the blood flow through the branching vessel. Additionally, once the surgeon determines the desired length of the segment of the blood vessel required for the bypass procedure, the ends of the blood vessel segment must be severed and cauterized as well before the blood vessel segment is extracted from the patient's body.

The extraction procedure can range from minimally to highly invasive. A highly invasive extraction procedure typically requires an incision long enough to extract the blood vessel segment having the desired length. Such an incision can result in severe post operative pain to the patient and often can lead to long term or permanent numbness of the extraction site.

A minimally invasive extraction procedure, e.g., for a saphenous vein, typically begins with a relatively small incision formed in the patient's leg to create an opening into the patient's leg at the first end of the saphenous vein segment. Working under the patient's skin, the surgeon then uses multiple tools to sever and cauterize branching vessels and connective tissue to isolate the saphenous vein segment. After sufficient isolation, a second relatively small incision is formed in the patient's leg to create an opening into the patient's leg at the second end of the saphenous vein segment. The first and second ends of the saphenous vein segment are then severed and cauterized to allow the surgeon to extract the saphenous vein segment from the patient's leg.

The number of steps, and the resulting number of tools, required to extract a blood vessel can make performing the minimally invasive procedure difficult for an inexperienced surgeon. The amount of connective tissue present, the number of branching vessels, and the length of the required segment of the blood vessel can make the procedure highly time consuming.

Thus, it would be desirable to provide a medical device to allow a surgeon to isolate a segment of the blood vessel using a single instrument to avoid exchanging multiple instruments during the procedure. Further, it would be desirable if such medical instrument is capable of grasping and/or cauterizing branching vessels and/or connective tissue independently of any cutting action to allow a surgeon to more effectively and efficiently navigate the device under the skin along the length of the blood vessel.

BRIEF SUMMARY

In one embodiment, a surgical instrument is provided. The instrument can be suitable for navigating under the skin along the saphenous vein of a patient to isolate the saphenous vein from branching vessels and/or connective tissue so that the saphenous vein may be harvested for use in CABG surgery. The instrument can include a tubular member with an outer wall defining a lumen that extends longitudinally through the tubular member. A grasper can extend within the tubular member. The grasper can include two grasping members. Each grasping member can include a distal body. Each distal body can have an inner surface facing the inner surface of the other distal body. The inner surface can include an opening. The grasping members can be pivotally coupled to one another at a first pivot point. The grasping members can be movable to rotate relative to one another about the first pivot point between an open configuration and a closed configuration. A cutting device can extend within the tubular member. The cutting device can include a cutting member and a cutting device shaft coupled to the cutting member. The cutting member can have at least one cutting edge configured to sever a body vessel and/or body tissue. Axial movement of the cutting device shaft relative to the tubular member can cause the cutting member to move between a free configuration and an engaged configuration. When the grasping members are in the closed configuration, the inner surfaces of the distal bodies can be in abutting contact with one another, and the openings of the distal bodies can form a cavity to receive the cutting member. The distal bodies can be configured to shield the cutting member during navigation of the instrument through the body.

In another embodiment, a method of removing branching vessels or connective tissue from a segment of a blood vessel is provided. The method can include introducing a surgical instrument into a body of a patient. The instrument can include a grasper and a cutting device. The grasper can include first and second grasping members. The grasping members can be pivotally coupled to one another. The grasping members also can be movable relative to one another between a closed configuration and an open configuration. The cutting device can include first and second cutting members. The cutting members can be pivotally coupled to one another. The cutting members also can be movable relative to one another between an engaged configuration and a free configuration. The grasping members can be movable between the open and closed configurations independently of any movement of the cutting members. When the grasping members are in the closed configuration, the grasping members can be configured to shield the cutting members for navigation through the body of the patient. The method also can include translating the grasper and the cutting device to a target branching vessel or connective tissue. The target branching vessel or connective tissue may be engaged by moving the grasping members from the open configuration toward the closed configuration. The engaged target branching vessel or connective tissue may be severed by moving the cutting members from the free configuration toward the engaged configuration.

BRIEF DESCRIPTION OF THE DRAWINGS

FIG. 2 is a perspective view of the distal portion of the instrument with the grasping members in the closed configuration and the cutting members in the engaged configuration.

FIG. 3 is a perspective view of the distal portion of the instrument with the grasping members in the open configuration and the cutting members in the free configuration.

FIG. 4a is a top view of the grasper with the grasping members in the closed configuration.

FIG. 4b is a top view of the grasper with the grasping members in the open configuration.

FIG. 5a is a top view of the cutting device with the cutting members in the engaged configuration.

FIG. 5b is a top view of the cutting device with the cutting members in the free configuration.

FIG. 5c is a top view of the cutting device illustrating the grasping members (shown in phantom lines) configured to shield the cutting members.

DETAILED DESCRIPTION OF THE DRAWINGS AND THE PRESENTLY PREFERRED EMBODIMENTS

Figure 1:
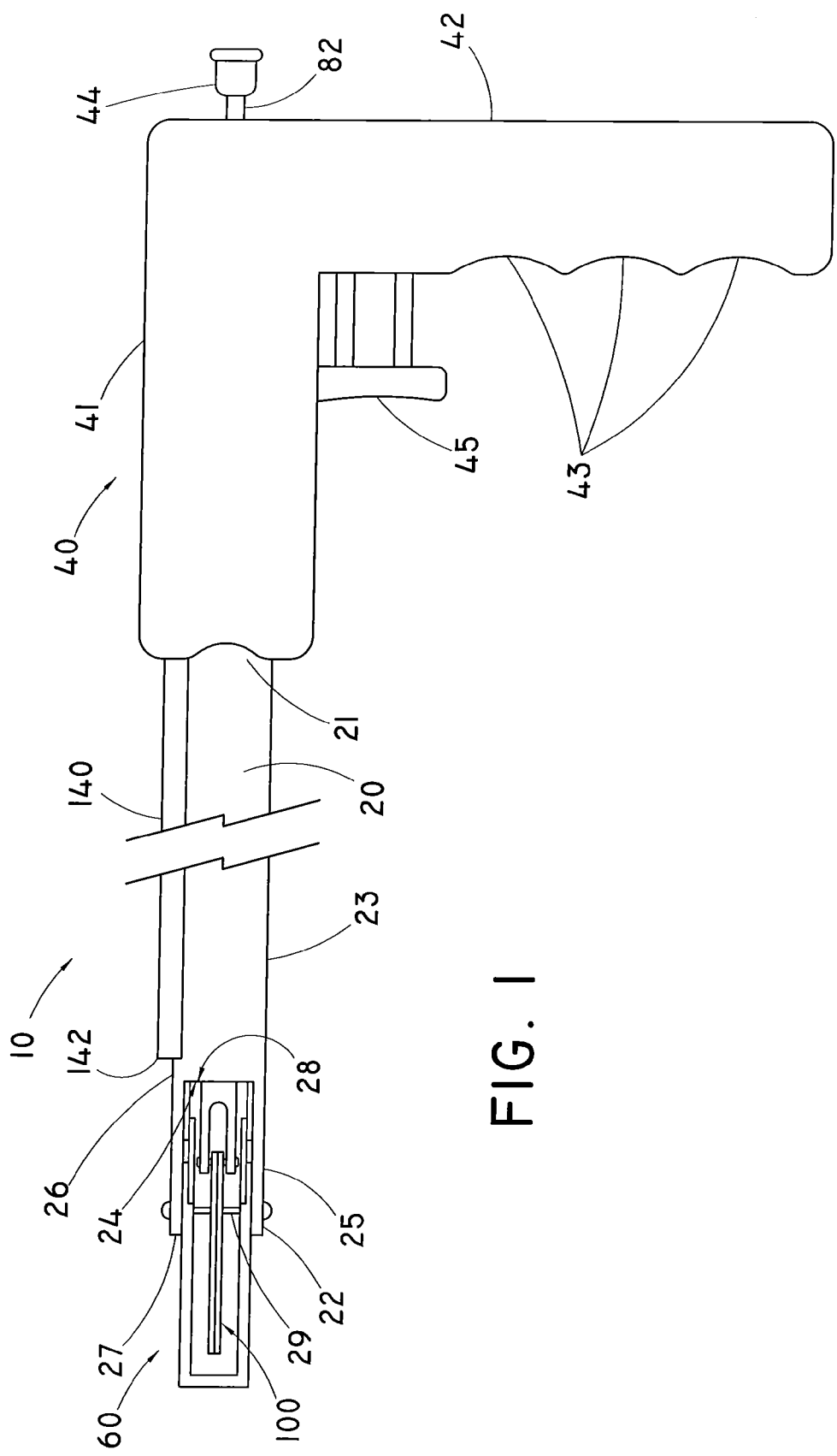
FIG. 1 is a side elevation view of a surgical instrument according to the present disclosure.

For the purposes of promoting an understanding of the principles of the present disclosure, reference will now be made to the embodiments illustrated in the drawings, and specific language will be used to describe the same.

In the following discussion, the terms "proximal" and "distal" will be used to describe the opposing axial ends of the inventive instrument, as well as the axial ends of various component features. The term "proximal" is used in its conventional sense to refer to the end of the instrument (or component thereof) that is closest to the operator during use of the instrument. The term "distal" is used in its conventional sense to refer to the end of the instrument (or component thereof) that is initially inserted into the patient, or that is closest to the patient during use.

Generally speaking, the present disclosure is directed to a surgical instrument. The instrument may be used to isolate a segment of a body vessel such as a blood vessel from branching vessels and/or connective tissue to prepare the blood vessel segment for extraction from a patient's body. FIGS. 1-3 illustrate an exemplary surgical instrument 10. The instrument 10 can include a tubular member 20 disposed about a general longitudinal axis of the device. The tubular member 20 has a proximal portion 21 and a distal portion 22. The tubular member 20 further can include an outer wall 23 defining at least one lumen 24 that extends longitudinally through the tubular member 20. The lumen 24 can be configured for receiving a grasper 60 and a cutting device 100 as further described herein. An entire cross sectional area of the lumen 24 may be filled to effectively separate and/or seal at least a portion of the lumen 24 from an interior portion of the body of the patient. For example, a grasper actuating member and/or a cutting device actuating member may occupy substantially an entire cross sectional area of the lumen 24 as shown in FIG. 3. Alternatively, a gap may be formed within the lumen 24 between the grasper actuating member and/or the cutting device actuating member and the wall 23 of the tubular member 20. A fork member 25 may be disposed at a distal end of the tubular member 20. The fork member 25 has a proximal end 26 and a distal end 27. The fork member 25 can include at least one notched opening 28 in the outer wall 23 of the tubular member 20. The instrument 10 can further include a handle 40. The handle 40 can be generally L-shaped. The handle 40 can be coupled to the proximal portion 21 of the tubular member 20. A barrel member 41 of the handle 40 may extend longitudinally and proximally from the proximal portion 21 of the tubular member 20. A hollow portion of the barrel member 41 can be in communication with the lumen 24 of the tubular member 20. The handle 40 can further include a grip member 42 coupled to the barrel member 41. The grip member 42 can be disposed in a perpendicular orientation with respect to the barrel member 41. The grip member 42 can have at least one finger indentation 43 for receiving an operator's fingers during operation of the instrument 10. The handle 40 can further include a thumb button 44 and a trigger 45 for operating the instrument 10 as further described herein.

FIGS. 2-3 illustrate the distal portion 22 of the tubular member 20 of the instrument 10. The grasper 60 can include grasping members 61 and 61'. The grasping member 61' can be a mirror image of the grasping member 61. Because the features of the grasping member 61 and the grasping member 61' can be identical, the description herein is confined to the grasping member 61. It will be readily recognized by one skilled in the art that any description of the grasping member 61 can apply equally to the grasping member 61'.

The grasping member 61 can have a distal body 62 with a central cavity 63 formed therein. The central cavity 63 can extend laterally within the distal body 62 from an inner surface 67. The central cavity 63 may extend entirely through a width of the distal body 62 so that the distal body has a U-shape formed by a distal end 69 interconnecting two distal body elongate portions 62A and 62B as shown in FIG. 3. The distal end 69 can be configured as an atraumatic tip to facilitate navigation through the patient's body. For example, the distal end 69 can have a blunt end shaped rectangularly or in the form of other geometric shapes such as conical or tapered. The distal body elongate portions 62A, 62B can be separated from one another by the cavity 63. Alternatively, the central cavity 63 may not extend entirely through the width of the distal body 62, thus forming a recess that leaves a solid portion of the distal body 62 along an outer surface 68 of the distal body 62. The inner surface 67 can be generally U-shaped with the central cavity 63 forming the central void of the U-shape.

With additional reference to FIGS. 4a-4b, the grasping member 61 can have at least one proximal tab member 64 coupled to a proximal end of the distal body 62, e.g., the proximal ends of the distal body elongate portions 62A, 62B. In one example, the at least one proximal tab member 64 may include two proximal tab members. One of the two proximal tab members may be coupled to the distal body elongate portion 62A, and the other may be coupled to the distal body elongate portion 62B as shown in FIGS. 1-3. In another example, a single proximal tab member may be coupled to one or both of the distal body elongate portions 62A, 62B. Returning to FIGS. 4a-4b, the distal body 62 extends generally in the longitudinal direction. The proximal tab member 64 may be oriented relative to the distal body 62 to extend obliquely with respect to the inner surface 67 and/or the outer surface 68 of the distal body 62.

A first pivot point A can be disposed at an end 65 of the proximal tab member 64 proximate to the distal body 62. Each of the grasping members 61, 61' can be pivotally coupled to the fork member 25 of the tubular member 20 at the first pivot point A. The first pivot point A can be fixed in relation to the tubular member 20. In one example, the first pivot point A can be fixed in relation to the tubular member 20 such that the grasping member 61 can rotate about the first pivot point A, without the grasping member 61 translating longitudinally relative to the tubular member 20. The grasping members 61, 61' further can be pivotally coupled to one another at the first pivot point A. The grasping members 61 and/or 61' can be caused to rotate about the first pivot point A, which rotation may be in opposite directions relative to one another as further described herein. The ability of the grasping members 61, 61' to move between the open and closed configurations without relative longitudinal translation may allow the grasper 60 to be employed to engage a body vessel and/or connective tissue without a physician being required to reposition the instrument 10 to compensate for any longitudinal movement of the grasper 60. Additionally, such ability may decrease the probability of unintentionally damaging a body vessel and/or connective tissue during use of the grasper 60 by avoiding sliding movement of the grasping members 61, 61' against the body vessel and/or connective tissue.

As shown in FIG. 2, the distal body 62 can extend distally beyond the distal end 27 of the fork member 25. In one illustrative example, the distal body 62 may extend from about 0.5 inches to about 1.5 inches beyond the distal end 27 of the fork member 25. The distal end 27 of the fork member 25 may be tapered to provide a generally smooth transition from the distal body 62 to the outer wall 23 of the tubular member 20 to facilitate navigation of the tubular member 20 within a patient's body. The proximal end 26 of the fork member 25 also may be tapered to provide a generally smooth transition from the notched opening 28 to the outer wall 23 of the tubular member 20.

The instrument 10 may include a cautery system 70 to cauterize a body vessel or body tissue. The cautery system can include one or more electrodes, e.g., a first electrode 71 and a second electrode 72, as shown in FIG. 3. The electrodes can be configured to receive high frequency energy for cauterizing a body vessel or body tissue. The electrodes can extend longitudinally along a length of the distal body 62 of the grasping member 61. For example, the electrodes 71, 72 can be disposed on the inner surface 67 of the distal body 62 such that the electrodes and the inner surface can be substantially coplanar.

In one example, the first electrode 71 may be disposed along the elongate portion 62A and the second electrode 72 may be disposed along the elongate portion 62B of the distal body 62. The first electrode 71 and the second electrode 72 can be separated by the central cavity 63 of the distal body 62 by a distance shown as a distance G. Consequently, a first cauterization made with the first electrode 71 and a second cauterization made with the second electrode 72 can be separated by the distance G. The distance G can be dimensioned such that a sufficient length can remain between the first cauterization and the second cauterization to allow a cauterized body vessel or body tissue to be severed between the first and second cauterizations without disturbing the first and/or second cauterizations. In one illustrative example, the distance G may range from about 0.3 inches to about 1 inch. High frequency energy for cauterizing a body vessel or body tissue may be provided by any means known in the art. As a non-limiting example, high frequency energy may be provided by the Model GC High Frequency Cautery Set available from Hospital Equipment Depot. The first electrode 71 and the second electrode 72 may be constructed of a conductive metal capable of carrying sufficient energy to cauterize a body vessel and/or body tissue. As a non-limiting example, one such conductive metal is gold.

FIGS. 4a-4b illustrate the grasper 60, with the grasping members 61, 61' in a closed configuration (FIG. 4a) and an open configuration (FIG. 4b). In the closed configuration, the distal bodies 62, 62' can be in abutting contact with one another at the inner surface 67 along a longitudinal axis P of the grasper, as shown in FIG. 4a. In the open configuration, the distal bodies 62, 62' can have a maximum angle of separation H relative to the axis P, as shown in FIG. 4b. In one illustrative example, the angle H may range from about 10 degrees to about 25 degrees for a total angle of separation between the distal bodies 62, 62' of from about 20 degrees to about 50 degrees. A grasper actuating member 80 can extend within the lumen 24 of the tubular member 20. The grasper actuating member 80 can include a grasper actuating shaft 81 having a proximal end 82 (within the handle 40) and a distal end 83. The grasper actuating member 80 further can include two actuating arms 84, 84'. A first end of each of the grasper actuating arms 84, 84' can be pivotally coupled to the distal end 83 of the grasper actuating shaft 81 at a second pivot point B. The first and second pivot points A, B can remain oriented along the axis P. A second end of the grasper actuating arm 84 can be pivotally coupled to a proximal end of the proximal tab member 64 of the grasping member 61 at a third pivot point C. A second end of the grasper actuating arm 84' can be pivotally coupled to a proximal end of the proximal tab member 64' of the grasping member 61' at a fourth pivot point D. The third and fourth pivot points C, D can be separated from the axis P by substantially equal distances and disposed longitudinally between the first and second pivot points.

The grasper actuating member 80 can be configured such that longitudinal movement of the grasper actuating shaft 81 along the axis P causes movement of the grasping members 61, 61' between the closed and open configurations. For example, the grasper actuating shaft 81 can be in a first longitudinal position to cause the grasping members 61, 61' to be in the closed configuration. When the grasping members 61, 61' are in the closed configuration, as shown in FIG. 4a, the first pivot point A and the second pivot point B are at their farthest proximity from one another, while the third pivot point C and the fourth pivot point D are at their closest proximity to one another. The grasper actuating shaft 81 can be moved distally toward a second longitudinal position to cause the grasping members 61, 61' to move toward the open configuration. As the grasping members 61, 61' move toward the open configuration, as shown in FIG. 4b, the first pivot point A remains fixed and the second pivot point B is moved closer to the first pivot point A along the axis P, while the third pivot point C and the fourth pivot point D are moved farther away from one another and from the axis P. As a result, the actuating arms 84, 84' can be moved distally, while pivoting outward with respect to the axis P about the second pivot point B. Consequently, the second ends of the actuating arms 84, 84' urge the grasping members 61, 61' to rotate about the first pivot point A toward the open configuration. Return movement of the grasping members 61, 61' to the closed configuration can be accomplished in reverse order.

Actuation of the grasper actuating shaft 81, and thus movement of the grasping members 61, 61' between the closed and open configurations, can be performed by manually moving the grasper actuating shaft 81 or by activating a control member. For example, the grasper actuating shaft 81 can be operatively coupled to the thumb button 44 of the handle 40. Activation of the thumb button 44 can cause longitudinal movement of the grasper actuating shaft 81. A spring or other biasing member known in the art (not shown) may bias the grasper actuating shaft 81 and/or the grasping members 61, 61' in either configuration. In one example, the spring biases the grasper actuating shaft 81 in the first position and thus the grasping members 61, 61' in the closed configuration.

Returning to FIG. 2, the cutting device 100 can include various cutting members that are configured to cut through body vessels and/or tissues, such as blood vessels and/or connective tissues. In one such example a cutting member 101 can include an elongate body having a proximal end 102 and a distal tip 103. With additional reference to FIGS. 5a-5c, the cutting member 101 can include a cutting edge 104. At least a portion of the cutting edge 104 can be configured to sever a body vessel or body tissue. An outer edge 105, opposite the cutting edge, can be configured to be atraumatic, such as being rounded or dulled. A fifth pivot point E can be disposed between the proximal end 102 and the distal tip 103 so that the cutting member 101 can rotate about the fifth pivot point E as further described herein. The cutting member 101 can be pivotally coupled to the fork member 25 of the tubular member 20 at the fifth pivot point E. The fifth pivot point E can be fixed in relation to the tubular member 20 such that the cutting member 101 can rotate about the fifth pivot point E, without translating longitudinally relative to the tubular member 20. The ability of the cutting member 101 to move between the free and engaged configurations without translating longitudinally may allow the cutting device 100 to sever a body vessel and/or connective tissue without a physician being required to reposition the instrument 10 to compensate for any longitudinal movement of the cutting device 100. Additionally, such ability may decrease the probability of unintentionally damaging a body vessel and/or connective tissue during use of the cutting device 100 by avoiding sliding movement of the cutting member 101 against the body vessel and/or connective tissue. The cutting member 101 can extend distally beyond the distal end 27 of the fork member 25.

The cutting device 100 further can include a cutting member 101'. The cutting member 101' can be a mirror image of the cutting member 101. Because the features of the cutting member 101 and the cutting member 101' can be identical, the description herein is confined to the cutting member 101. It will be readily recognized by one skilled in the art that any description of the cutting member 101 can apply equally to the cutting member 101'. The cutting members 101, 101' can be pivotally coupled to one another at the fifth pivot point E to form a scissor structure.

The first pivot point A and the fifth pivot point E can be aligned along a common axis. For example, a rod 29 can be fixed to the fork member 25 of the tubular member 20 as shown in FIG. 1. The rod 29 can extend transversely across the lumen 24 of the tubular member 20. The rod 29 may be oriented in a perpendicular relationship with respect to the axis P of the grasper 60 and/or the axis R of the cutting device 100. The grasping members 61, 61' may be pivotally coupled to the rod 29 at the first pivot point A. The cutting members 101, 101' may be pivotally coupled to the rod 29 at the fifth pivot point E. The first pivot point A and the fifth pivot point E may be positioned along the rod 29 such that the grasping members 61, 61' and the cutting members 101, 101' rotate about an axis defined by the rod 29.

FIGS. 5a-5c illustrate one example of the cutting device 100. The cutting members 101, 101' can rotate about the fifth pivot point E in opposite directions relative to one another between the engaged configuration and the free configuration. In the engaged configuration, the cutting edges 104 and 104' can engage one another as shown in FIG. 5a to sever a body vessel or body tissue disposed therebetween. In the free configuration, the cutting edges 104 and 104' can have a maximum angle of separation I from the axis R as shown in FIG. 5b. In one illustrative example, the angle I may range from about 10 degrees to about 25 degrees for a total angle of separation between the cutting members 101, 101' of from about 20 degrees to about 50 degrees.

The cutting member 101 can include an elongate opening 107 formed therein. The elongate opening 107 can extend along the cutting member 101 from the proximal end 102 to a position adjacent the fifth pivot point E. The elongate opening 107 can be angled to terminate closer to the outer edge 105 than the cutting edge 104. A proximal end 108 of the elongate opening 107 can be generally centered on a width of the cutting member 101 at the proximal end 102. A distal end 109 of the elongate opening 107 can be disposed generally between the fifth pivot point E and the outer edge 105 of the cutting member 101. The elongate openings 107, 107' can be angled in opposite directions relative to one another when the cutting members 101, 101' are pivotally coupled to one another as shown in FIG. 5a.

A cutting device actuating member 120 can extend within the lumen 24 of the tubular member 20 along the axis R. The cutting device actuating member 120 can include a cutting device actuating shaft 121 having a proximal end 122 (within the handle 40) and a distal end 123. The cutting device actuating member 120 further can include an actuating pin 124. The actuating pin 124 can be configured to slidably engage the elongate openings 107, 107' and to move longitudinally between the proximal and distal ends of the elongate openings. The pin 124 can remain substantially along the longitudinal axis R during movement. The elongate opening 107 can be angled such that longitudinal movement of the actuating pin 124 within the elongate opening 107 can cause the cutting member 101 to rotate about the fifth pivot point E.

The cutting device actuating member 120 can be configured such that longitudinal movement of the cutting device actuating shaft 121 causes movement of the cutting members 101, 101' between the engaged configuration and the free configuration. For example, the cutting device actuating shaft 121 can be in a first longitudinal position to cause the cutting members 101, 101' to be in the engaged configuration, where the cutting edges may be in an abutting relationship along the axis R, as shown in FIG. 5a. In this position, the pin 124 is positioned at the proximal ends of the elongate openings along the axis R, farthest away from the fifth pivot point E. The cutting device actuating shaft 121 can be moved distally toward a second longitudinal position to cause the actuating pin 124 to move distally along the axis R within the elongate openings 107, 107' closer to the fifth pivot point E. The fifth pivot point E may remain in a fixed location. As a result, the proximal ends are urged away from the axis R, and the cutting members 101, 101' rotate about the fifth pivot point E toward the free configuration, as shown in FIG. 5b. Return movement of the cutting members 101, 101' toward the engaged configuration can be accomplished in reverse order.

Actuation of the cutting device actuating shaft 121, and thus movement of the cutting members 101, 101' between the engaged and free configurations, can be performed by manually moving the shaft or activating a control member. For example, the cutting device actuating shaft 121 can be operatively coupled to the trigger 45 of the handle 40. Activation of the trigger 45 can cause longitudinal movement of the cutting device actuating shaft 121. A spring or other biasing member known in the art (not shown) may bias the cutting device actuating shaft 121 and/or the cutting members 101, 101' in either configuration. In one example, the spring biases the cutting device actuating shaft 121 toward the first position and the cutting members 101, 101' toward the engaged configuration.

Returning to FIG. 2, at least a portion of the cutting member 101 can be disposed substantially within the central cavity 63 of the distal body 62. As shown in FIG. 5c, the distal tip 103 of the cutting member 101 can remain disposed within the central cavity 63 of the grasping member 61 (shown in phantom lines) regardless of whether the cutting member 101 is in the engaged configuration or the free configuration to reduce any potential risk of inadvertently puncturing or severing a body vessel or body tissue. The grasping members 61, 61', when in the closed configuration, can form a protective housing substantially surrounding the cutting member 101, as shown in FIGS. 2 and 5c. To this end, the grasping members can shield the cutting member 101 to reduce any potential risk of inadvertently puncturing or severing a body vessel or body tissue. Preferably, the grasping members 61, 61' can be biased toward the closed configuration to form the protective housing to allow the distal portion 22 of the tubular member 20 to be more effectively and efficiently navigated through the body of the patient.

The grasping member 61 can extend beyond the distal tip 103 of the cutting member 101 by a distance F, as shown in FIG. 2. The distance F can be dimensioned such that the grasper 60 may be capable of grasping and/or cauterizing a body vessel or body tissue independently of movement and/or position of the cutting members 101, 101'. For example, the grasper 60 may be capable of engaging and/or cauterizing a body vessel or body tissue regardless of whether the cutting members 101, 101' are in the free configuration or the engaged configuration and without the need to move the cutting device 100 longitudinally from a fixed location with respect to the tubular member 20. To this end, the body vessel or body tissue may be engaged between the grasping members 61, 61' within the distance F such that contact between the body vessel or body tissue and the cutting members 101, 101' may be avoided. Consequently, the grasper 60 may be used to more effectively and efficiently navigate the tubular member 20 among various obstacles or obstructions within a patient's body. For example, the grasper 60 may be capable of pushing an obstacle or obstruction to the side or cauterizing the obstacle or obstruction to remove it from the path of the tubular member 20. In one illustrative example, the distance F may be greater than about 0.25 inches. In another illustrative example, the distance F may range from about 0.3 inches to about 0.7 inches.

An endoscope port 140 can be disposed within or exterior to the tubular member 20. The endoscope port 140 can define an endoscope lumen 141 formed therein. The endoscope lumen 141 can be configured to receive an endoscope or other medical imaging device known in the art (not shown). The endoscope lumen 141 can be disposed substantially parallel with respect to the lumen 24 of the tubular member 20. Preferably, a distal end 142 of the endoscope port 140 can be disposed such that a region substantially surrounding the distal portion 22 of the tubular member 20 may be visible from the distal end 142. Preferably, the distal end 142 of the endoscope port 140 can be disposed such that at least a portion of the grasping member 61 and the cutting member 101 may be visible from the distal end 142. The endoscope port 140 further can include a clear protective shield (not shown) over the distal end 142 to protect the endoscope or other medical imaging device received within the endoscope lumen 141 from becoming obstructed by debris.

During use of the surgical instrument 10 for isolating a blood vessel segment from branching vessels and/or connective tissue, the distal portion 22 of the tubular member 20 can be inserted percutaneously into the body of the patient in conventional manner, and under real time visualization. Preferably, the manner of visualization can be an endoscope or other medical imaging device received within the endoscope port 140. However, any other methods of visualization that are capable of providing suitable images may be utilized. At the time of insertion, the grasping members 61, 61' can be in the closed configuration of FIG. 4a to form a blunt, atraumatic tip. Likewise, the cutting members 101, 101' can be in the engaged configuration of FIG. 5a. The protective housing formed by the grasping members 61, 61' in the closed configuration can substantially surround the cutting members 101, 101' to protect the patient from unintentional punctures or incisions during insertion of the distal portion 22 of the tubular member 20. The distal portion 22 can be navigated along a blood vessel until a branching vessel or connective tissue is encountered. During navigation of the distal portion 22, the grasper 60 can be operated independently of the cutting device 100 to move various body tissues or other obstacles from the path of the distal portion 22 to more effectively and efficiently navigate the distal portion 22 along the blood vessel. The protective housing formed by the grasping members 61, 61' can continue to protect the patient from unintentional punctures or incisions during navigation of the distal portion 22 along the blood vessel.

Once the distal portion 22 of the tubular member 20 has reached a target branching vessel or connective tissue, the target branching vessel or connective tissue can be cauterized and/or severed to isolate the blood vessel. For example, the thumb button 44 can be activated to cause the grasping members 61, 61' to move from the closed configuration to the open configuration. The trigger 45 can be activated to cause the cutting members 101, 101' to move from the engaged configuration to the free configuration. The distal portion 22 of the tubular member 20 can be advanced into a position such that the target branching vessel or connective tissue is disposed between the grasping members 61, 61' and between the cutting members 101, 101'. The thumb button 44 can be released to cause the grasping members 61, 61' to move from the open configuration toward the closed configuration to engage the target branching vessel or connective tissue between the grasping members 61, 61'. The inner surfaces of the grasping members can be in abutting contact with the engaged target branching vessel or connective tissue. When present, the electrodes 71, 72 can be caused to receive high frequency energy to cauterize the target branching vessel or connective tissue engaged by the grasping members 61, 61'. Such high frequency energy may be provided by any means known in the art. Additionally, such high frequency energy may be activated by any means known in the art. As a non-limiting example, the high frequency energy may be activated by activating a foot pedal. The trigger 45 can be released to cause the cutting members 101, 101' to move from the free configuration to the engaged configuration to sever the target branching vessel or connective tissue engaged by the grasping members 61, 61'. The target branching vessel or connective tissue may be severed in a region between the cauterization made by the first electrodes and the cauterization made by the second electrodes. The thumb button 44 can be activated to cause the grasping members 61, 61' to move from the closed configuration to the open configuration to disengage the severed branching vessel or connective tissue. The distal portion 22 of the tubular member 20 can be advanced into a position such that the severed branching vessel or connective tissue is no longer disposed between the grasping members 61, 61' or between the cutting members 101, 101'. The thumb button 44 can be released to cause the grasping members 61, 61' to move from the open configuration to the closed configuration. The foregoing procedure as herein described can be repeated until the blood vessel segment of desired length has been isolated from branching vessels and/or connective tissue. Once the blood vessel segment has been isolated, the distal portion 22 may be retracted from the body of the patient.

The blood vessel segment may then be extracted from the body of the patient for use in CABG surgery using any method known in the art. For example, a proximal end of the blood vessel segment may be cauterized and severed. An incision may be made to expose a distal end of the blood vessel segment. The distal end of the blood vessel segment may be cauterized and severed. Finally, the blood vessel segment may be extracted from the patient's body through the incision near the proximal end of the blood vessel segment or the incision near the distal end of the blood vessel segment.

It is intended that the foregoing detailed description of the medical devices and methods be regarded as illustrative rather than limiting, and that it be understood that it is the following claims, including all equivalents, that are intended to define the spirit and scope of this invention. Terms are to be given their reasonable plain and ordinary meaning. Also, the embodiment of any figure and features thereof may be combined with the embodiments depicted in other figures. Other features known in the art and not inconsistent with the structure and function of the present invention may be added to the embodiments.

Drawings in the figures illustrating various embodiments are not necessarily to scale. Some drawings may have certain details magnified for emphasis, and any different numbers or proportions of parts should not be read as limiting, unless so-designated in the present disclosure. Those skilled in the art will appreciate that embodiments not expressly illustrated herein may be practiced within the scope of the present invention, including those features described herein for different embodiments, and may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

The invention claimed is:

1. A surgical instrument comprising:
    a tubular member having a proximal end, a distal end, and at least one lumen extending between the proximal end and the distal end;
    a grasper extending within a lumen of the tubular member, the grasper comprising first and second grasping members each having a distal body, each distal body having an inner surface with an opening formed therein, the inner surfaces of the first and second grasping members facing one another, the grasping members pivotally coupled to one another at a first pivot point to move about the first pivot point between an open configuration and a closed configuration;
    a cutting device extending within a lumen of the tubular member, the cutting device having first and second cutting members each with at least one cutting edge configured to sever a body vessel or tissue, the first and second cutting members being pivotally coupled to one another at a second pivot point to move about the second pivot point between a free configuration and an engaged configuration; and
    a rod coupled to the tubular member and extending transversely across a lumen of the tubular member,
    wherein the first and second grasping members are pivotally coupled to the rod at the first pivot point, the first and second cutting members are pivotally coupled to the rod at the second pivot point, and the first and second grasping members and the first and second cutting members are configured to pivot about an axis of the rod; and
    wherein the grasping members are movable between the open and closed configurations independent of movement of the cutting members between the free and engaged configurations.

2. The instrument of claim 1, wherein the grasper further comprises a grasper shaft pivotally coupled to the first and second grasping members, wherein relative axial movement of the grasper shaft moves the first and second grasping members relative to one another about the first pivot point.

3. The instrument of claim 2, wherein the cutting device further comprises a cutting device shaft coupled to an actuating pin, wherein each of the cutting members comprises an elongate opening configured to receive the actuating pin and longitudinal movement of the actuating pin within the elongate openings causes the cutting members to rotate about the second pivot point relative to one another between the free configuration and the engaged configuration.

4. The instrument of claim 1, wherein, when the grasping members are in the closed configuration, the inner surfaces of the distal bodies of the grasping members are in an abutting relationship, and the openings of the distal bodies form a cavity to receive the cutting members, and, when the grasping members are in the closed or open configuration, the distal bodies of the grasping members are configured to shield the cutting members during movement of the cutting members between the free and engaged configurations.

5. The instrument of claim 4, wherein, during movement of the cutting members between the free and engaged configurations, distal tips of the cutting members are disposed within the openings of the distal bodies of the grasping members.

6. The instrument of claim 1, the grasper further comprising a grasper shaft and each of the first and second grasping members further comprising at least one proximal tab member, wherein proximal tab members of the first and second grasping members are pivotally coupled to one another and pivotally coupled to the grasper shaft and relative axial movement of the grasper shaft rotates the first and second grasping members relative to one another about the first pivot point between the open configuration and the closed configuration.

7. The instrument of claim 1, wherein each of the distal bodies has a distal end, the distal ends of the distal bodies of the grasping members, individually or in combination with one another, are configured to form an atraumatic tip of the instrument.

8. The instrument of claim 1, wherein a distal end of the distal body of each of the grasping members extends a distance beyond the distal tip of the cutting member.

9. The instrument of claim 1, wherein the grasper further comprises a first electrode disposed on the distal body of each of the grasping members, the first electrode configured to cauterize the body vessel or tissue.

10. The instrument of claim 9, wherein the grasper further comprises a second electrode disposed on the distal body of each of the grasping members, wherein the first and second electrodes are separated by the opening of the inner surface of the distal body.

11. The instrument of claim 1, wherein the cutting device further comprises a cutting device shaft coupled to an actuating pin, wherein each of the cutting members comprises an elongate opening configured to receive the actuating pin and longitudinal movement of the actuating pin within the elongate openings causes the cutting members to rotate about the second pivot point relative to one another between the free configuration and the engaged configuration.

12. The instrument of claim 1, further comprising an endoscope port to receive a medical imaging device, the endoscope port disposed along an outer wall of the tubular member.

13. A method of removing branching vessels or connective tissue from a blood vessel, the method comprising:
    introducing a surgical instrument comprising a grasper, a cutting device and a rod into a body of a patient, the grasper comprising first and second grasping members pivotally coupled to one another and movable relative to one another between a closed configuration and an open configuration, the cutting device comprising first and second cutting members pivotally coupled to one another and movable relative to one another between an engaged configuration and a free configuration, wherein the first and second grasping members are pivotally coupled to the rod at a first pivot point, the first and second cutting members are pivotally coupled to the rod at a second pivot point, and the first and second grasping members and the first and second cutting members are configured to pivot about an axis of the rod, wherein the grasping members are movable between the open and closed configurations independent of movement of the cutting members, and, when the grasping members are in the closed configuration, the grasping members are configured to shield the cutting members for navigation of the instrument through the body;
    translating the grasper and the cutting device to a target branching vessel or connective tissue;
    moving the grasping members from the open configuration to position the target branching vessel or connective tissue between the grasping members toward the closed configuration to engage the target branching vessel or connective tissue with the grasping members; and
    moving the cutting members from the free configuration to position the target branching vessel or connective tissue between the cutting members toward the engaged configuration to sever the target branching vessel or connective tissue with the cutting members.

14. The method of claim 13, each of the first and second grasping members comprising a distal body having an inner surface with an opening formed therein, wherein the grasping members are biased in the closed configuration, and, when the grasping members are in the closed configuration, the inner surfaces of the distal bodies are in an abutting relationship and the openings of the distal bodies form a cavity to receive the cutting members.

15. The method of claim 13, wherein the first and second cutting members are disposed and movable within the openings of the first and second grasping members.

16. The method of claim 13, wherein the grasping members and the cutting members are secured in a longitudinally fixed relationship with respect to the tubular member to prevent axial movement of the grasping members and the cutting members during pivotal movement of the respective grasping members and the cutting members.

* * * * *